United States Patent [19]
DeMaio et al.

[11] Patent Number: 5,540,798
[45] Date of Patent: Jul. 30, 1996

[54] BALLOON CATHETER

[76] Inventors: Samuel J. DeMaio, 4309 Overhill, Dallas, Tex. 75205; Paul J. Durfee, 510 Maumee Rd., Waxahachie, Tex. 75165

[21] Appl. No.: 382,509

[22] Filed: Feb. 2, 1995

[51] Int. Cl.⁶ ........................................ B32B 31/00
[52] U.S. Cl. ................ 156/200; 156/218; 156/463; 156/465; 604/280
[58] Field of Search ........................... 156/200, 203, 156/217, 218, 465, 466, 467, 483, 477.1, 463; 604/43, 280

[56] References Cited

U.S. PATENT DOCUMENTS

| | | | |
|---|---|---|---|
| 4,636,272 | 1/1987 | Riggs | 156/158 |
| 4,642,152 | 2/1987 | Chapin | 156/218 X |
| 5,135,599 | 8/1992 | Martin et al. | 604/43 X |
| 5,405,472 | 4/1995 | Leone | 156/218 |

*Primary Examiner*—James Engel
*Attorney, Agent, or Firm*—William Lloyd Clayborn; John M. Cone

[57] ABSTRACT

The shaft of a dilation balloon catheter includes three lumens; a dilation balloon lumen, a guidewire lumen, and an inner balloon lumen. A dilation balloon near the distal near the distal end of the catheter is inflated and deflated through the dilation balloon lumen. An inner balloon within the guidewire lumen provides a means for releasably securing a guidewire disposed within the guidewire lumen, thereby allowing the catheter to be configured as a fixed-wire catheter and an over-the-wire catheter. The inner balloon is inflated and deflated through the inner balloon lumen. A longitudinally-extending separable area in the wall of the guidewire lumen allows the guidewire to pass transversely therethrough, thereby allowing the catheter to be removed from a patient while leaving the guidewire in place within the patient. A method for constructing the shaft is also provided.

3 Claims, 2 Drawing Sheets

BALLOON CATHETER

BACKGROUND OF THE INVENTION

The invention relates to the field of vascular catheters. More particularly, the invention is related to a dilation balloon catheter for use and percutaneous transluminal coronary angioplasty ("PTCA").

PTCA is an efficient and effective method for treating stenoses in coronary arteries. In a typical PTCA procedure, a guide catheter having a pre-shaped distal end is introduced into the patient's cardiovascular system through a femoral or brachial artery. Prior to introducing the guide catheter into the patient, a wire is inserted into the guide catheter to straighten the curved distal end of the catheter. Using fluoroscopy, the surgeon advances the guide catheter into the patient's aorta until the catheter's tip is adjacent to a desired branch artery. The wire is then withdrawn and the tip of the guide catheter engages the ostium of the desired branch artery. A dilation balloon catheter is passed through the guide catheter and into the branch artery. The balloon catheter is maneuvered to place the balloon within the stenosis to be treated. The balloon is inflated and deflated one or more times to compact the stenosis, then removed from the patient. Compacting the stenosis increases the diameter of the passage through the stenosis, thereby increasing the blood flow in the artery.

The most frequently used balloon catheter is the over-the-wire type. An over-the-wire catheter includes a guidewire lumen which extends from the proximal end of the catheter to the distal end. In use, a guidewire is slidably disposed in the guidewire lumen, and the catheter is inserted into and advanced to the distal end of the guide catheter. The guidewire is maneuvered along the patient's artery in order to pass the distal end of the guidewire through the stenosis to be treated. Finally, the catheter is advanced to place the balloon within the stenosis.

Over-the-wire balloon catheters have several inherent advantages. Over-the-wire catheters are quite "pushable," a characteristic which enables the surgeon to apply the force necessary to push the balloon though a tight stenosis. Also, it is possible to leave a guidewire in place within a stenosis while exchanging one over-the-wire catheter for another. Leaving a guidewire in place when exchanging catheters eliminates the need to again maneuver a guidewire's distal end through the stenosis, thereby saving time and decreasing the possibility of causing trauma to the patient. However, since the guidewire is contained within the catheter, for such an exchange to be accomplished, the guidewire's length must be increased to at least twice the length of the catheter. In one known procedure, an extension is added to the proximal end of the original guidewire to achieve adequate guidewire length. In another known procedure, the original catheter is left in place within the stenosis, or advanced as close as possible to the stenosis, and the original guidewire removed and replaced with an "exchange" guidewire of adequate length. Unfortunately, both of these procedures are cumbersome and require two operators to perform.

In some cases, a surgeon may find it is necessary to apply another device (such as a directional atherectomy device, a rotoblation device, or a stent) to a stenosis after using a balloon catheter. Since each of these devices requires a different type of guidewire, another advantage of an over-the-wire catheter is that the surgeon can remove the catheter's guidewire and replace it with another device's guidewire. Using one of the procedures described above, the surgeon can then remove the balloon catheter and replace it with the device. Again, exchanging guidewires eliminates the need to maneuver the device's guidewire to the stenosis to be treated. However, since one of the procedures for providing adequate guidewire length must be performed, replacing a balloon catheter with a device requires two operators.

Another conventional dilation balloon catheter is the fixed-wire type. The fixed-wire balloon catheter includes a short guidewire attached to and extending from the distal tip of the catheter. A fixed-wire catheter is inherently quite steerable, and hence relatively easy to maneuver to the stenosis to be treated. However, fixed-wire balloon catheters are not as pushable as the over-the-wire type. In addition, if it is necessary to change catheters, the new catheter must again be maneuvered to the stenosis to be treated, which requires additional time and increases the risk of trauma.

Rapid exchange catheters, such as that disclosed in U.S. Pat. No. 5,346,505 (Leopold), can be exchanged while leaving the guidewire in place in the patient without using an exchange wire or an extension wire. However, since the guidewire lumen of the catheter extends only a short distance proximally from the distal end of the catheter, the catheter cannot be used to position another guidewire across to the stenosis to be treated. Thus, while one rapid exchange catheter can easily be easily exchanged for another, changing from a rapid exchange catheter to another device requires removal of both the catheter and its guidewire before insertion of the device's guidewire.

SUMMARY OF THE INVENTION

The invention provides a dilation balloon catheter having the advantages of fixed-wire, over-the-wire, and rapid exchange catheters, without any of their disadvantages.

A preferred embodiment of the balloon catheter of the invention comprises an elongated shaft having a dilation balloon adjacent to its distal end. A dilation balloon lumen extends from the proximal end of the shaft and is in fluid communication with the dilation balloon. The dilation balloon lumen is used to inflate and deflate the dilation balloon.

A guidewire lumen within the shaft extends from the proximal end of the shaft to the distal end of the shaft. The guidewire lumen is adapted to receive a guidewire in a sliding relationship.

An inner balloon is disposed within the distal portion of the guidewire lumen. The inner balloon is inflated and deflated by means of an inner balloon lumen which extends from the proximal end of the shaft. When the inner balloon is deflated, the guidewire is free to slide relative to the shaft. When the inner balloon is inflated, the guidewire's position is fixed relative to the shaft.

A portion of the guidewire lumen wall can be separated to allow a guidewire to be moved transversely into or out of the guidewire lumen. The separable portion of the guidewire lumen wall extends longitudinally from near the proximal end of the shaft to near the distal end of the shaft. This feature of allows the catheter of the invention to act as a rapid exchange catheter. That is, without using a guidewire extension or an exchange length guidewire, the catheters of the invention can be exchanged by one person while maintaining the guidewire's position within the patient. Further, the separable portion of the guidewire lumen wall is resilient, and it tends to return to its original closed position when not held apart by a transversely-moving guidewire. As a result, the catheter of the invention can be left in position within the patient to guide the guidewire of another device to the stenosis to be treated, then removed by one person without moving the new guidewire.

In a preferred method of constructing the catheter of the invention, the shaft is formed from a long, narrow, transversely-tapered sheet of polyurethane (the "shaft sheet"). The dilation balloon lumen is formed by applying glue to the longitudinally-extending, thick edge of the sheet, then pulling the sheet through an appropriately-shaped, heated die. The inner balloon lumen is formed by gluing the longitudinally-extending edges of a long, thin, narrow sheet of polyurethane to what will become the inner surface of the shaft. The inner balloon is formed by gluing the four edges of a very thin, flexible, rectangular sheet of polyurethane over the distal end of the inner balloon lumen and to what will become the inner surface of the shaft. Glue is applied the proximal and distal portions of the longitudinally-extending, thin edge of the shaft sheet. The shaft sheet is then drawn through an appropriately-shaped, heated die to form the final, generally tubular shape of the shaft. The portion of the thin edge to which glue was not applied forms the separable portion of the guidewire lumen wall.

BRIEF DESCRIPTION OF THE DRAWINGS

An embodiment of the invention will be described, by way of example only, with reference to the accompanying drawings, in which.

DETAILED DESCRIPTION

Figure 1:
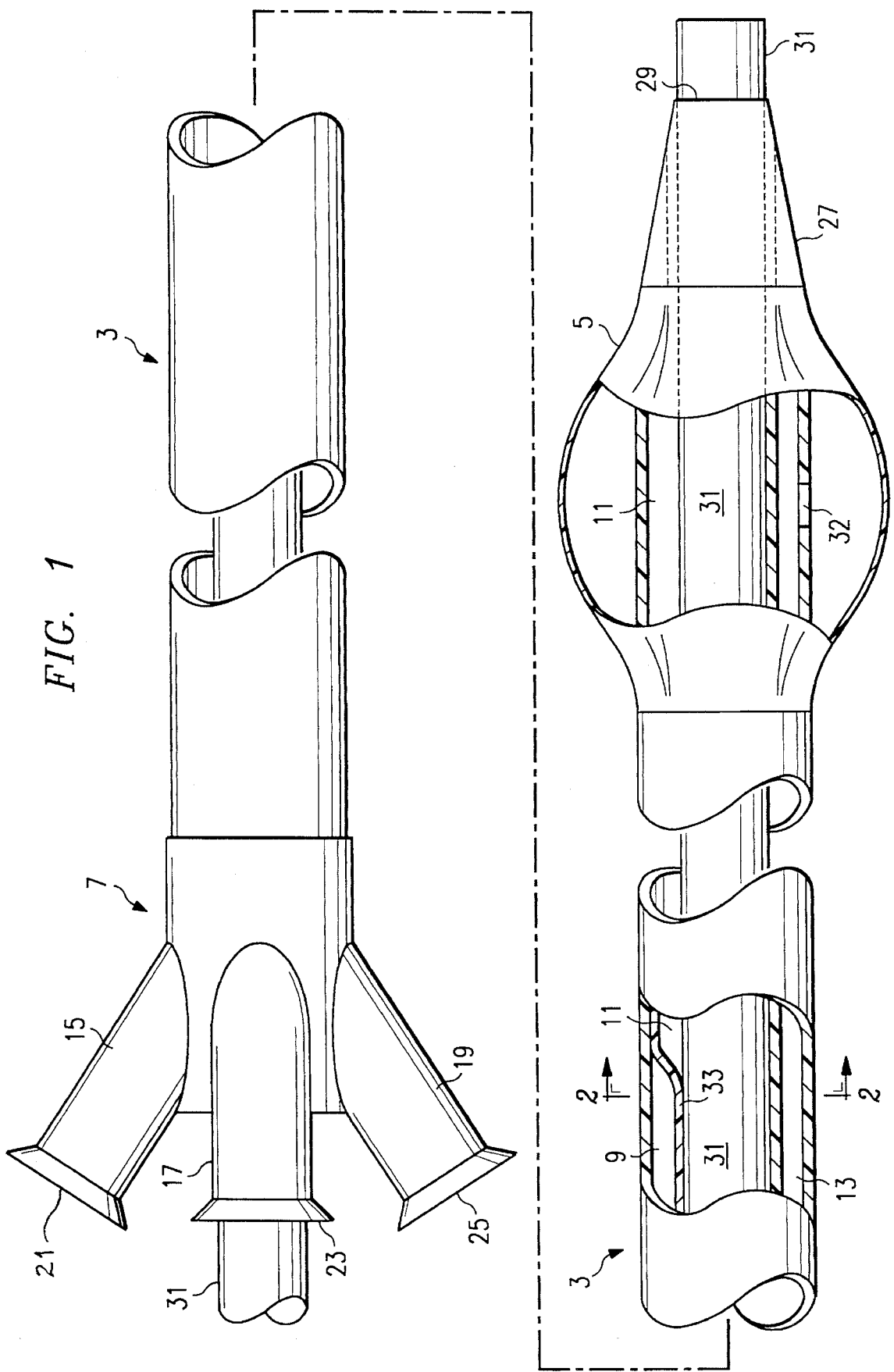
FIG. 1 is a partially-cutaway side view of a balloon catheter in accordance with the invention.
Figure 2:
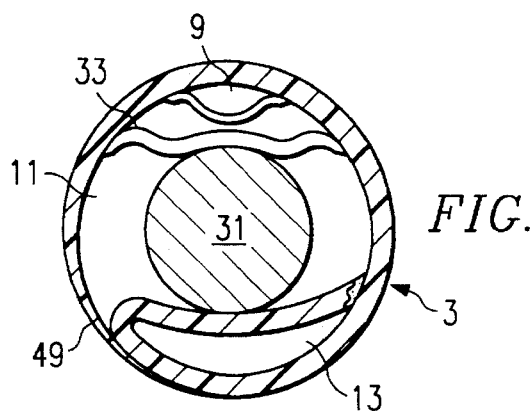
FIG. 2 is a cross-sectional view taken through plane 2—2 in FIG. 1.

FIGS. 1–3 illustrate a dilation balloon catheter 1 embodying the invention. Referring first to FIG. 1, the catheter 1 comprises a tubular member 3 (the "shaft") having an external dilation balloon 5 on the distal portion thereof. A three-port hub 7 connected to the proximal end of the shaft 3 provides access to three lumens 9, 11, 13: an inner balloon lumen 9, a guidewire lumen 11, and a dilation balloon lumen 13. The top port 15 of the hub 7 is connected to the inner balloon lumen 9, the center port 17 is connected to the guide wire lumen 11, and the bottom port 19 is connected to the dilation balloon lumen 13. The proximal ends of the ports 15, 17, 19 each includes a conventional connector 21, 23, 25, respectively, such as a Luer fitting.

The guidewire lumen 11 extends from the center port 17 of the hub 9 to the distal end of the catheter 1. At the distal end of the catheter 1, a tapered tip 27 is joined to the distal end of the shaft 3 by conventional means, such as gluing. An orifice 29 is provided in the tapered tip 27 to allow a guidewire 31 to pass therethrough. The tapered tip 27 seals the distal end of the dilation balloon lumen 13 to prevent leakage of fluid therefrom. The tapered tip 27 also provides a smooth transition from the shaft 3 to the guide wire 31 in order to avoid damage to vascular tissue by the distal end of the catheter 1.

The conventional dilation balloon 5 (shown inflated in FIG. 1) is attached to the exterior surface of the shaft 3 by conventional means, such as gluing or bonding. To inflate the dilation balloon 5, a source of pressurized fluid (not shown) is connected to the connector 25 on the lower port 19 of the hub 7. The pressurized fluid passes through the lower port 19, the dilation balloon lumen 13, an orifice 32 near the distal end of the dilation balloon lumen 13, and into the dilation balloon 5. The dilation balloon 5 is deflated by applying a vacuum source (not shown) to the lower port 19 of the hub 7.

An inner balloon 33 at the distal end of the inner balloon lumen 9 can be inflated or deflated by attaching a source of pressurized fluid or vacuum, respectively, to the connector 21 on the upper port 15 of the hub 7. The inner balloon 33 is shown deflated in FIG. 1 and inflated in FIG. 2. When the inner balloon 33 is deflated, the guidewire 31 can slide freely in the guidewire lumen 11, allowing the catheter 1 to be used as an over-the-wire catheter. Inflating the inner balloon 41 fixes the guidewire 31 within the guidewire lumen 9, allowing the catheter 1 to be used as a fixed-wire catheter.

Figure 3A:
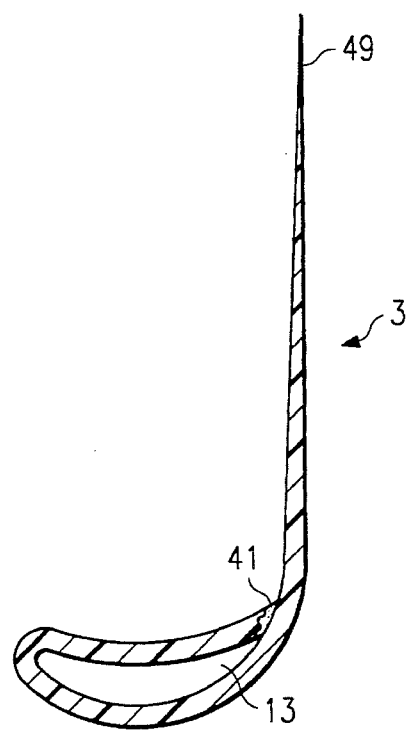
FIGS. 3a–3c are cross-sectional views illustrating the method of constructing the shaft of the catheter of FIG. 1.
Figure 3B:
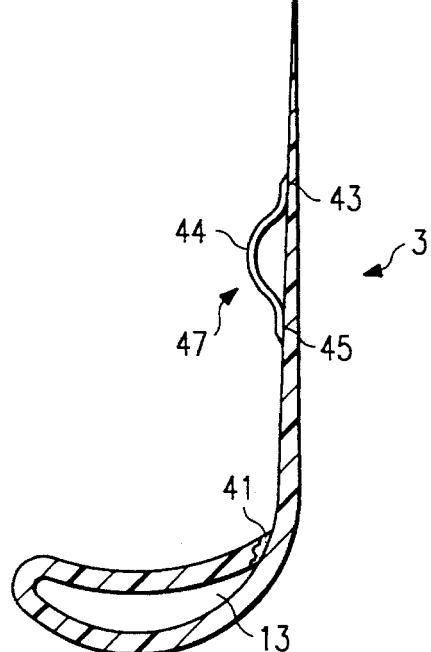
Figure 3C:
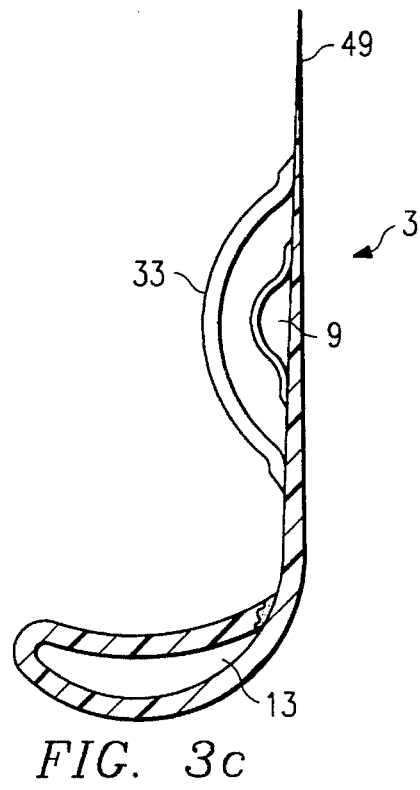

FIGS. 3a–3c illustrate a preferred method for constructing the shaft 3 of the catheter 1. The shaft 3 is constructed of a long (approximately 130 cm), narrow sheet of polyurethane (the "shaft sheet"). The sheet is tapered In cross-section. Glue is applied to the longitudinally-extending, thick edge 41 of the sheet and the sheet is pulled through a heated die to form the shape shown in FIG. 3a and thereby form the dilation balloon lumen 13. As illustrated in FIG. 3b, the longitudinal edges 43, 45 of a long, narrow, thin sheet of polyurethane 47 are then glued to what will become the inside surface of the shaft 3. As can be seen, a small hump 49 in the sheet 47 forms the inner balloon lumen 9. As illustrated in FIG. 3c, the inner balloon 33 is then formed at the distal end of the inner balloon lumen 9 by gluing the four edges of a very thin, flexible, rectangular sheet of polyurethane over the distal end of the inner balloon lumen 9 and to what become the inside surface of the shaft 3. Finally, glue is applied to the distal 30 cm and proximal 30 cm of the thinner edge 49 of the sheet, and the sheet is pulled through a heated die to form the shape shown in FIG. 2, thereby forming the guidewire lumen 11. The shape of the heated die is adjusted to taper the shaft 3 inwardly from the distal edge of the inner balloon 33 to the distal end of the shaft 3. This decreases the cross-sectional area of the distal portion of the catheter 1, allowing treatment of smaller-diameter stenoses than would otherwise be the case.

After the construction step which forms the guidewire lumen 11, the wall of the distal 30 cm and proximal 30 cm of the guidewire lumen 11 is overlapped and glued, while the wall of the center approximately 70 cm of the guidewire lumen 9 is merely overlapped. If the shaft 3 is grasped over the portion of the wall of the guidewire lumen 11 which is only overlapped (the "separable area") and bent sharply in the direction away from separable area, the wall of the guidewire lumen 11 will open, and the guidewire 31 can be pushed or pulled transversely through the opening. Due to the resiliency of the separable area, the wall of the guidewire lumen 11 will return to its original closed position when not held open by the guidewire 31.

Prior to beginning the angioplasty procedure, a petcock (not shown) is connected to the connector 23 on the upper port 17 of the hub 9. To ensure that the guidewire balloon 41 is completely deflated, a vacuum source (not shown) is connected to the petcock, and the petcock is opened. The guidewire 31 is inserted into center port 19 of the hub 9, and pushed through the dilation catheter 1 until the guidewire 31 is adjacent to the distal end of the catheter 1. If the catheter 1 is to be configured as an over-the-wire catheter, the petcock is closed, and the vacuum source is removed. If the catheter 1 is to be configured as a fixed-wire catheter, the guidewire 31 is pushed until its distal end extends approximately 1–2 cm distally of the tapered tip 27. The vacuum source is removed, and a source of pressurized fluid is connected to the petcock. The pressurized fluid inflates the guidewire balloon 41, securing the guidewire 31 in place within the guidewire lumen 11. Finally, the petcock is closed to maintain the inflation of the guidewire balloon 41, and the source of pressurized fluid is disconnected from the petcock.

As with prior art balloon catheters, a guide catheter (not shown) is first introduced into the patient through one of the patient's femoral or brachial arteries. After maneuvering the guide catheter so that its distal tip engages the ostium of the desired coronary artery, the catheter 1 is inserted into the guide catheter. The surgeon then proceeds as with a conventional over-the-wire catheter or fixed-wire catheter, depending on how the catheter 1 is configured. Of course, the surgeon can reconfigure the catheter 1 at any time utilizing the petcock and a vacuum or pressure source, as appropriate.

To change the catheter 1 while leaving the guidewire 31 in the patient, the catheter 1 is first configured as an over-the-wire catheter, if necessary. Then, while holding the proximal end of the guidewire 31 to fix the guidewire's position relative to the patient, the proximal end of the catheter 1 is pulled out of the patient to expose the beginning of the separable area of the wall of the guidewire lumen 11. Grasping the shaft 3 over the separable area, the surgeon bends the shaft 3 sharply away from the separable area. While maintaining the bend in the shaft 3, the surgeon pushes on the proximal end of the guidewire 31, thereby causing a portion of the guidewire 31 to move transversely out of the guidewire lumen 11. While firmly grasping the shaft 3 distally of where the guidewire 31 extends through the wall of the guidewire lumen 11, the surgeon pulls on the exposed guidewire 31 until the proximal end of the guidewire 31 exits the wall of the guidewire lumen 11. Next, the surgeon grasps the guidewire 31 with one hand to hold the guidewire 31 immobile relative to the patient, grasps the shaft 3 proximally to the guidewire 31, and pulls the shaft 3 proximally until the guidewire 31 approaches the distal end of the separable area. The surgeon then moves the hand holding the guidewire 31 proximally a sufficient distance to allow the distal end of the catheter 1 to be pulled out of the guide catheter (not shown) with the other hand. Finally, the surgeon grasps the guidewire 31 distally of the distal end of the catheter 1 with one hand, while pulling the catheter 1 proximally to remove it from the guidewire 31. In this manner, the catheter 1 is removed while leaving the distal end of the guidewire 31 in place through the stenosis. Installation of a catheter 1 is the reverse of removal.

With the catheter i configured as an over-the-wire catheter (the inner balloon 33 is deflated), exchanging guidewire 31 without moving the catheter 1 relative to the patient can be easily accomplished. With one hand, the surgeon grasps the catheter 1 to immobilize it relative to the patient. With the other hand, the surgeon removes the guidewire 31 from the catheter 1. The new guidewire can then be inserted into the catheter 1 through the center port 17 of the hub 7. If the reason for exchanging guidewires 31 is that the catheter 1 is to be replaced by another device, after the distal end of the new guidewire 31 is through the stenosis to be treated, the catheter 1 removed as described above.

While the preferred embodiments of the catheter and construction method of invention have been shown and described, it will be apparent to those skilled in this art that various modifications may be made to these embodiments without departing from the spirit of the invention.

We claim:

1. A method for constructing a shaft for a dilation balloon catheter comprising the steps of:
   a. applying an adhesive agent to a first longitudinally-extending edge of a sheet of plastic material;
   b. applying a first die to the sheet, the first die being shaped to cause the first edge of the sheet to contact a surface of the sheet partway between the first edge of the sheet and a second opposed edge of the sheet, thereby forming a first lumen;
   c. applying an adhesive agent to a portion of the second edge of the sheet; and
   d. applying a second die to the sheet, the second die being shaped to cause the second edge of the sheet to contact an outer surface of the first lumen, thereby forming a second lumen.

2. The method of claim 1 further comprising the step of adhering two longitudinally-extending opposed edges of a second sheet of plastic material to a surface of the first sheet.

3. The method of claim 1 wherein, in a least one of steps 1(*b*) and 1(*d*), the die is heated.

\* \* \* \* \*